United States Patent [19]

Guentner et al.

[11] Patent Number: 4,958,021
[45] Date of Patent: * Sep. 18, 1990

[54] BENZOPYRAN DERIVATIVES

[75] Inventors: Andreas Guentner; Udo Mayer, both of Frankenthal; Andreas Oberlinner, Ludwigshafen, all of Fed. Rep. of Germany

[73] Assignee: BASF Aktiengesellschaft, Ludwigshafen, Fed. Rep. of Germany

[*] Notice: The portion of the term of this patent subsequent to Jun. 20, 2006 has been disclaimed.

[21] Appl. No.: 221,268

[22] Filed: Jul. 19, 1988

[30] Foreign Application Priority Data

Jul. 25, 1987 [DE] Fed. Rep. of Germany ....... 3724757

[51] Int. Cl.$^5$ ............... C07D 311/00; C07D 311/58; C07D 405/04; C07D 405/06
[52] U.S. Cl. ..................... 544/129; 544/130; 544/131; 544/143; 544/151; 546/135; 546/194; 546/196; 548/374; 548/455; 548/524; 548/525; 549/398; 549/399; 549/404; 549/407; 549/408
[58] Field of Search ............... 549/407, 398, 399, 404, 549/408; 544/143, 151, 150, 353, 129-131, 140; 546/196, 135, 194; 548/455, 525, 374, 524

[56] References Cited

U.S. PATENT DOCUMENTS

| 2,800,457 | 7/1957 | Green et al. | 428/402.2 |
| 2,800,458 | 7/1957 | Green et al. | 428/402.2 |
| 3,103,404 | 9/1963 | Salvin et al. | 8/464 |
| 3,843,384 | 10/1974 | Adachi et al. | 543/201 |
| 3,872,023 | 3/1975 | Baum et al. | 428/402.22 |
| 3,896,112 | 8/1975 | Kubota et al. | 549/403 |
| 4,183,553 | 1/1980 | Petitpierre | 549/404 X |
| 4,187,233 | 2/1980 | Petitpierre | 549/404 |
| 4,406,816 | 9/1983 | Sliwka | 521/69 |

FOREIGN PATENT DOCUMENTS 2413849 10/1975 Fed. Rep. of Germany ........ 311/82
2156909 2/1975 France .

OTHER PUBLICATIONS

Chemical Abstracts, 98(15), 125819d (1983).

Primary Examiner—Mary C. Lee
Assistant Examiner—M. S. Howard
Attorney, Agent, or Firm—Oblon, Spivak, McClelland, Maier & Neustadt

[57] ABSTRACT

Benzopyran derivatives of the formula

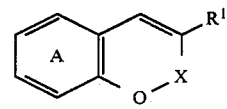

where X is the radical

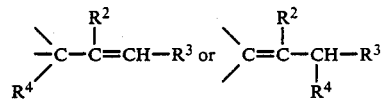

and $R^1$, $R^2$, $R^3$, $R^4$ and also the ring A have defined meanings are used in pressure- or heat-sensitive layers.

1 Claim, No Drawings

BENZOPYRAN DERIVATIVES

The present invention provides a novel benzopyran derivative of the formula I

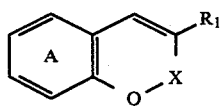
(I)

where $R^1$ is substituted or unsubstituted $C_1$–$C_8$-alkyl, substituted or unsubstituted phenyl, $C_1$–$C_5$-alkoxy or halogen and X is the radical

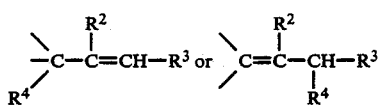

where $R^2$ is hydrogen or together with $R^1$ is unsubstituted or $C_1$–$C_4$-alkyl-substituted $C_2$–$C_3$-alkylene, $R^3$ is $C_1$–$C_4$-alkoxyphenyl whose alkyl radical is substituted by phenyl, $C_1$–$C_4$-mono- or -bis-(cyanoalkyl)aminophenyl, naphthyl which is substituted or N-($C_1$–$C_4$-alkyl)-N-phenylamino, 1- or 2-phenylindol-3-yl, the radical

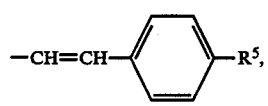

the radical

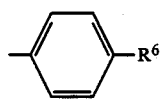

or
the radical

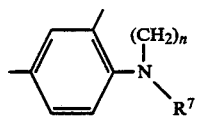

and $R^4$ is hydroxyl, $C_1$–$C_5$-alkoxy, substituted or unsubstituted phenoxy, substituted or unsubstituted phenylsulfonyl, pyrrolidino, piperidino, morpholino or the radical of an acidic CH compound and where the ring A may be fused with a benzo ring or substituted by $C_1$–$C_4$-alkyl, chlorine or bromine or, in ring position 7, by hydroxyl, $C_1$–$C_4$-alkoxy, $C_1$–$C_5$-mono- or dialkylamino (which in turn may be substituted by chlorine or phenyl), pyrrolidino, piperidino or morpholino, $R^5$ being $C_1$–$C_8$-alkyl, $C_1$–$C_8$-alkoxy, which each may be substituted by phenyl, or being $C_5$–$C_7$-cycloalkyl, $C_5$–$C_7$-cycloalkoxy, $C_1$–$C_4$-mono- or dialkylamino, phenylamino or N-($C_1$–$C_4$-alkyl)-N-phenylamino and $R^6$ being the radical

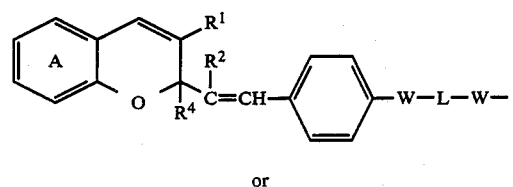

or

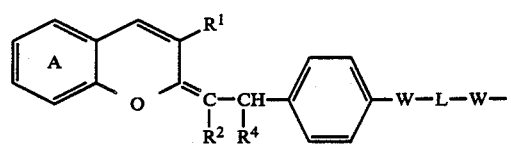

where $R^1$, $R^2$, $R^4$ and the ring A each have the abovementioned meanings, W is oxygen or $C_1$–$C_4$-alkylimino, and L is $C_2$–$C_6$-alkylene or

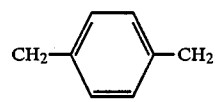

$R^7$ being $C_1$–$C_4$-alkyl and
n being 2 or 3,
with the proviso that when the ring A is unsubstituted and not benzofused and $R^1$ is methyl and X is the radical

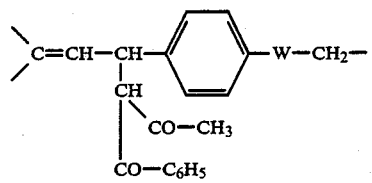

W is not ethylimino.

Benzopyran derivatives of similar structure are also described in the earlier application EP-A-236,973.

All the alkyl and alkylene groups appearing in the abovementioned radicals can be not only straight-chain but also branched.

$R^1$ in the formula I is for example methyl, ethyl, propyl, isopropyl, butyl, isobutyl, tert-butyl, pentyl, isopentyl, sec-pentyl, tert-pentyl, hexyl, heptyl, octyl or 2-ethylhexyl, phenyl, for example $C_1$–$C_4$-alkoxy- or halogen-substituted phenyl, such as 4-methylphenyl, 2-methylphenyl, 4-ethylphenyl, 4-isopropylphenyl, 4-methoxyphenyl, 2-ethoxyphenyl, 4-chlorophenyl or 2,4-dichlorophenyl, methoxy, ethoxy, propoxy, isopropoxy or butoxy, fluorine, chlorine or bromine.

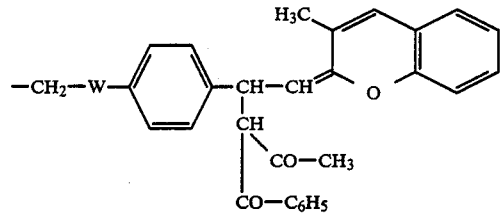

$R^2$ in the formula I is for example hydrogen or, together with $R^1$, 1,2-ethylene, 1,2-propylene, 1,3-propylene or 2-methyl-1,3-propylene.

$R^3$ in the formula I is for example 4-benzyloxyphenyl, 4-(1-phenylethoxy)phenyl, 4-(2-phenylethoxy)phenyl, 4-(bis(2-cyanoethyl)amino)phenyl, 4-methylaminonaphth-1-yl, 4-ethylaminonaphth-1-yl, 4-dimethylaminonaphth-1-yl, 4-diethylaminonaphth-1-yl, 4-diisopropylaminonaphth-1-yl, 4-dibutylaminonaphth-1-yl, 4-phenylaminonaphth-1-yl, 4-(N-methyl-N-phenylamino)naphth-1-yl, 4-(N-ethyl-N-phenylamino)-naphth-1-yl, 4-methylstyryl, 4-ethylstyryl, 4-isopropylstyryl, 4-butylstyryl, 4-isopentylstyryl, 4-hexylstyryl, 4-heptylstyryl, 4-octylstyryl, 4-(2-ethylhexyl)styryl, 4-benzylstyryl, 4-(2-phenylethyl)styryl, 4-methoxystyryl, 4-ethoxystyryl, 4-propoxystyryl, 4-butoxystyryl, 4-benzyloxystyryl, 4-(2-phenylethoxy)styryl, 4-cyclopentylstyryl, 4-cyclohexylstyryl, 4-cycloheptylstyryl, 4-cyclopentyloxystyryl, 4-cyclohexyloxystyryl, 4-cycloheptyloxystyryl, 4-methylaminostyryl, 4-ethylaminostyryl, 4-dimethylaminostyryl, 4-phenylaminostyryl, 4-(N-methyl-N-phenylamino)styryl or 4-(N-ethyl-N-phenylamino)styryl, 1-methyl-2,3-dihydroindol-5-yl, 1-ethyl-2,3-dihydroin-dol-5-yl, 1-methyl-1,2,3,4-tetrahydroquinolin-6-yl or 1-ethyl-1,2,3,4-tetrahydroquinolin-6-yl.

$R^4$ in formula I is for example hydroxyl, methoxy, ethoxy, propoxy, isopropoxy, sec-butoxy, pentyloxy, phenoxy, for example $C_1$-$C_4$-alkyl-, $C_1$-$C_4$-alkoxy- or halogen-substituted phenoxy, such as 2-methylphenoxy, 4-methylphenoxy, 3-methoxyphenoxy or 4-chlorophenoxy, phenylsulfonyl, for example $C_1$-$C_4$-alkyl- or halogen-substituted phenylsulfonyl, such as 4-methylphenylsulfonyl or 4-chlorophenylsulfonyl, pyrrolidino, piperidino or morpholino.

$R^4$ in the formula I is further the radical of an acidic CH compound. Radicals of acidic CH compounds are for example 2-(pyrrolidino, piperidino or morpholino)-cyclopent-1-en-1-yl or -cyclohex-1-en-1-yl, and cyclohexane-1,3-dion-2-yl which is unsubstituted or monosubstituted or disubstituted in ring position 5 by $C_1$-$C_4$-alkyl, such as cyclohexane-1,3-dion-2-yl, 5-methylcyclohexane-1,3- dion-2-yl, 5-ethylcyclohexane-1,3-dion-2-yl or 5,5-dimethylcyclohexane-1,3-dion-2-yl, benzoylmethyl, cyano, nitromethyl, 2,4,6-trihydroxypyrimid-5-yl, 1-phenyl-3-methylpyrazol-5-on-4-yl, 5-hydroxy-3,4-dichlorofuran-2-yloxy, and the radical

where Y and Z are identical or different and each is independently of the other acetyl, benzoyl, $C_1$-$C_5$-alkoxycarbonyl or cyano and where, if Y is cyano, Z can also be methyl, such as bis(acetyl)methyl, bis(benzoyl)methyl, bis(methoxycarbonyl)methyl, bis(ethoxycarbonyl)methyl, bis(cyano)methyl, acetylbenzoylmethyl, acetylmethoxycarbonylmethyl, benzoylethoxycarbonylmethyl, cyanomethoxycarbonylmethyl, cyanoethoxycarbonylmethyl or 1-cyanoeth-1-yl.

Ring A in the formula I may be substituted, for example, by chlorine or bromine in ring position 6 or 8 or by chlorine in ring positions 6 and 8. It may further be substituted in ring position 7, for example by methyl, ethyl, propyl, isopropyl, butyl, hydroxyl, methoxy, ethoxy, isopropoxy, methylamino, ethylamino, propylamino, isopropylamino, butylamino, benzylamino, 2-chloroethylamino, dimethylamino, diethylamino, dibutylamino, dibenzylamino, methylethylamino, pyrrolidino, piperidino or morpholino. It may also be benzofused for example as follows:

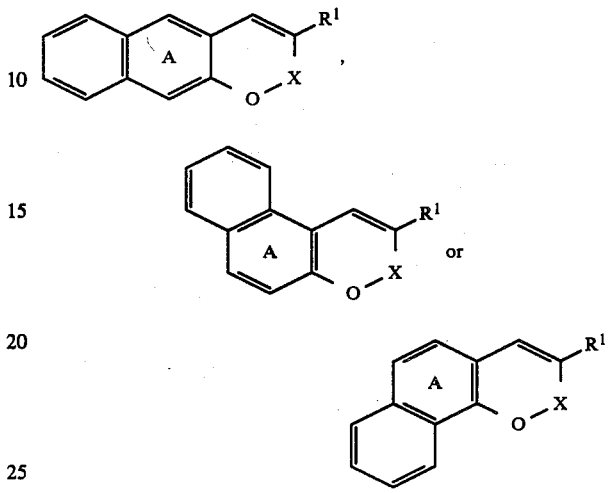

Preference is given to those benzopyran derivatives of the formula I where $R^1$ is $C_1$-$C_5$-alkyl, $R^2$ is hydrogen, $R^3$ is $C_1$-$C_4$-alkoxyphenyl whose alkyl is substituted by phenyl, and $R^4$ is the radical

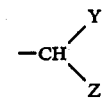

where Y and Z each have the abovementioned meanings.

Preference is further given to benzopyran derivatives of the formula I where $R^3$ is the radical

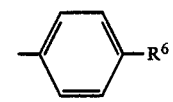

where $R^6$ has the abovementioned meanings, and W is oxygen.

The benzopyran derivatives according to the invention are advantageously obtained by reacting for example a benzopyrylium compound of the formula II

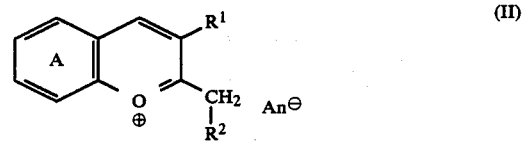 (II)

where $R^1$, $R^2$ and the ring A each have the abovementioned meanings and $An^\ominus$ is an anion, with an aldehyde of the formula III $R^3$—CHO  (III)

where $R^3$ has the abovementioned meanings, in a molar ratio of from 1:0.8 to 1:1.2 in the presence of an inert solvent at from 20° to 120° C., preferably at from 40° to 80° C., and, in a subsequent stage, making the resulting dye salt of the formula IV

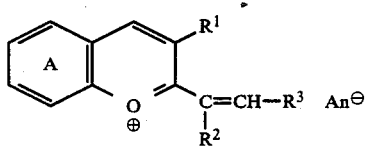

where $R^1$, $R^2$, $R^3$, $An^\ominus$ and the ring A each have the abovementioned meanings, react with a compound of the formula V $$R^4—H \qquad (V)$$

where $R^4$ has the abovementioned meanings, in a molar ratio of from 1:1.1 to 1:2 in the presence of an inert solvent and a base at from 20° to 120° C., preferably at from 40° to 80° C.

To prepare those compounds of the formula I where $R^3$ is the radical

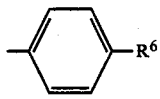

where $R^6$ has the abovementioned meanings, i.e. which have two benzopyran systems in the molecule, the benzopyrylium compound II is reacted first with a corresponding dialdehyde of the formula VI

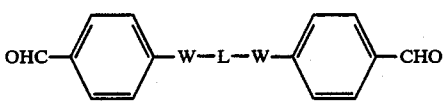

where L and W each have the abovementioned meanings, and then with a compound of the formula V. Here the particular molar ratios must allow for the fact that the compounds are bifunctional.

Suitable anions $An^\ominus$ are for example trichlorozincate, tetrachloroferrate(III), hydrogensulfate, nitrate and halide, such as chloride or bromide. Particular preference is given to trichlorozincate and tetrachloroferrate(III).

The inert solvent is advantageously an alcohol, for example, methanol, ethanol, propanol, isopropanol, butanol or isobutanol. If desired, it is also possible for the reaction medium to comprise mixtures of these alcohols with aromatic hydrocarbons, such as toluene or xylene.

Suitable bases for reacting the color salt IV with the compound V are for example alkali metal and alkaline earth metal carbonates, such as sodium carbonate, potassium carbonate, magnesium carbonate or calcium carbonate, alkaline earth metal oxides, such as magnesium oxide or calcium oxide, and alkali metal alkoxides, such as sodium methoxide, ethoxide or butoxide, or potassium methoxide, ethoxide or butoxide. In general, from 1 to 3 moles of base are added per mole of dye salt.

The necessary benzopyrylium salts II, aldehydes III and compounds IV for the process according to the invention are known.

The benzopyran derivatives according to the invention are slightly colored, if not colorless, compounds whose solutions in inert organic solvents produce on contact with electron acceptors, depending on the substituents on the benzopyran, colorings in yellow, orange, red, blue or green shades. Examples of electron acceptor substances are carboxylic or mineral acids, kaolin, bentonite, activated clay, aluminum silicate, attapulgite or any desired clay, acidic polymeric materials, such as condensation products based on phenols and/or phenolsulfonic acids, and also metal oxides or salts, such as zinc oxide, aluminum oxide, zinc chloride, iron stearate or cobalt naphthenate.

Owing to these properties, the novel compounds of the formula I are suitable for use as dye-forming components in pressure- and heat-sensitive recording materials.

For application in pressure-sensitive systems, the novel benzopyrans are microencapsulated, advantageously in the form of solutions in organic solvents, for example chloroparaffins, partially hydrogenated biphenyl or terphenyl, alkylbenzenes, alkylnaphthalenes, alkylated dibenzylbenzenes, paraffin oil, mineral oil or else customary low-boiling solvents, such as xylene or toluene, and the microcapsules are applied to the base material, for example paper. On the application of pressure, contact with electron acceptors then brings about dye formation at the point where pressure was applied.

Suitable processes for preparing microcapsules are known for example from U.S. Pat. No. 2,800,457, U.S. Pat. No. 2,800,458, DE-A-2,119,933 or EP-A-26,914. It is also possible to follow the process described in U.S. Pat. No. 3,103,404 and finely divide the compounds according to the invention in wax or oil-wax mixtures and to use these mixtures to coat base materials, such as films or paper. The results obtained are pressure-sensitive materials which are suitable for printing through on electron acceptor-coated paper and which, after use, are removed like carbon paper.

The benzopyrans according to the invention can also be used as dye-forming components in heat-sensitive recording materials containing on the base material a binder, a dye-forming component and an electron acceptor substance. The structure of such heat-sensitive recording materials and the composition of the layers which give rise to color on heating are known (for example DE-A-2,228,581 or DE-A-2,110,854), as are the processes and apparatus whereby color or dye formation is obtained.

The following Examples will illustrate the invention in more detail:

EXAMPLE 1 a. Synthesis of dye salt 33 g (0.1 mol) of 2,3-dimethylbenzopyrylium chlorozincate and 21 g (0.1 mol) of 4-benzyloxybenzaldehyde were refluxed in 100 ml of methanol for 4 hours. After cooling down, the precipitated dye was filtered off and washed with methanol.

Yield: 40 g (88% of theory)

Melting point: 235°–240° C. The dye salt obtained had the formula

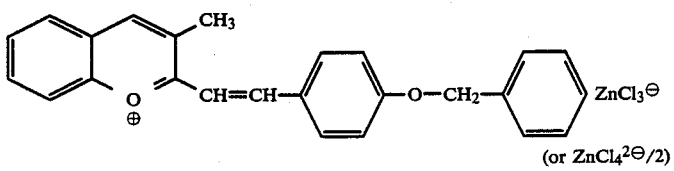

b. Synthesis of dye-forming component 13.7 g (0.03 mol) of the dye salt synthesized under a. and 4 g (0.04 mol) of acetylacetone were stirred in 150 ml of methanol at 45° C. in the presence of 7 g of sodium carbonate. The reaction mixture was poured into a mixture of 500 ml of toluene and 500 ml of water and stirred in. The organic phase was treated with active charcoal, filtered and evaporated under reduced pressure. On addition of 100 ml of methanol the residue formed crystals which it was possible to filter off with suction. Yield: 10 g (74% of theory)

The dye-forming component obtained had the formula

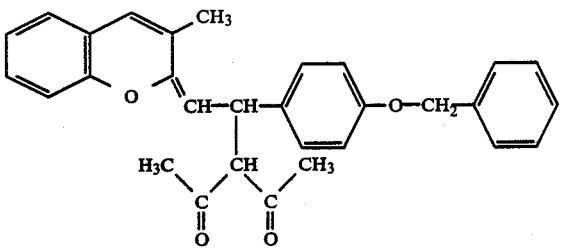

The compounds of the formula

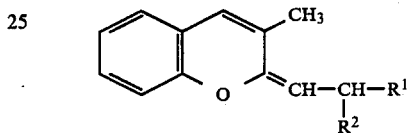

given in Table 1 below and the compounds listed in Table 2 are obtained in a similar manner.

TABLE 1

| Example No. | $R^1$ | $R^2$ | m.p. [°C.] | Color or λmax [nm] |
|---|---|---|---|---|
| 2 | —⌬—O—CH₂—⌬ | H₃C—C(=O)—CH—C(=O)—⌬ | 145–155 | 528 |
| 3 | —⌬—N(C₂H₄CN)₂ | H₃C—C(=O)—CH—C(=O)—CH₃ | 124–126 | 620 |
| 4 | —⌬—N(C₂H₄CN)₂ | ⌬—C(=O)—CH—C(=O)—⌬ | 235–240 | 620 |
| 5 | —⌬—N(C₂H₄CN)₂ | H₃C—C(=O)—CH—C(=O)—⌬ | 155–160 | 620 |
| 6 | 2-phenyl-3-methyl-indole | H₃C—C(=O)—CH—C(=O)—CH₃ | 136–138 | 596 |

TABLE 1-continued
| Example No. | R[1] | R[2] | m.p. [°C.] | Color or λmax [nm] |
|---|---|---|---|---|
| 7 | 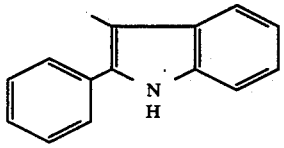 | 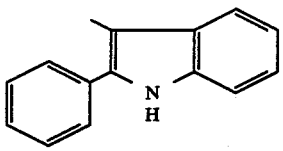 | 150–152 | 596 |
| 8 | 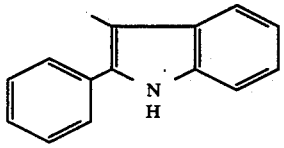 | 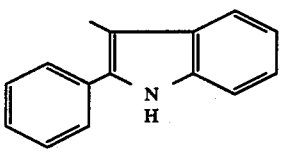 | 177–178 | 596 |
| 9 | 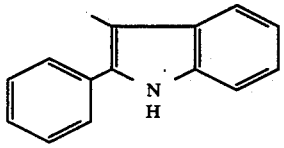 | 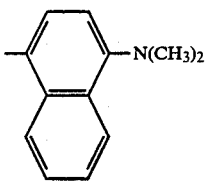 | 179–180 | 596 |
| 10 | 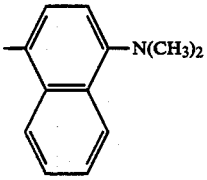 | 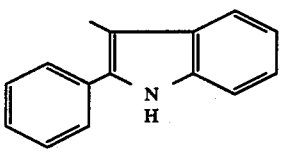 | 82–86 | blue |
| 11 | 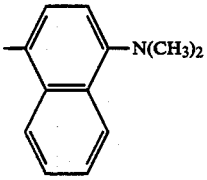 | 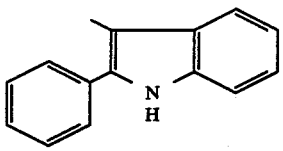 | 140–145 | blue |
TABLE 2
| Ex. No. | Formula | m.p. [°C.] | Color or λmax [nm] |
|---|---|---|---|
| 12 | 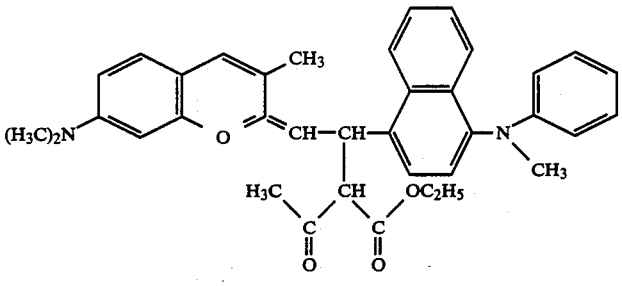 | 139–141 | gray |
| 13 | 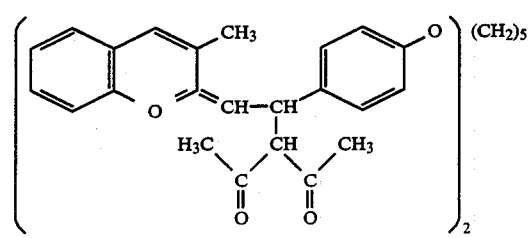 | oil | red |
We claim:
1. A benzopyran derivative of the formula I

[structure at top: benzo-fused ring A with =CH-R¹ and O-X]

where
R¹ is unsubstituted C₁–C₈-alkyl, phenyl, C₁–C₄-alkoxy or halogen-substituted phenyl, C₁–C₅-alkoxy or halogen and
X is the radical $$-\underset{R^4}{\overset{R^2}{C}}-\underset{|}{C}=CH-R^3 \quad \text{or} \quad \underset{/}{\overset{\backslash}{C}}=\underset{R^4}{\overset{R^2}{C}}-CH-R^3$$

where
R² is hydrogen or together with R¹ is unsubstituted or C₁–C₄-alkyl-substituted C₂–C₃-alkylene,
R³ is C₁–C₄-alkoxyphenyl whose alkyl radical is substituted by phenyl, C₁–C₄-mono- or -bis(cyanoalkyl) aminophenyl, naphthyl which is substituted by C₁–C₄-mono- or -di -alkylamino, phenylamino or N-(C₁–C₄-alkyl)-N-phenylamino, 1- or 2-phenylindol-3-yl, the radical —CH=CH—[phenyl]—R⁵, the radical —[phenyl]—R⁶ or
the radical

—[phenyl with ortho substituent]—N(CH₂)ₙ / R⁷ and
R⁴ is hydroxyl, C₁–C₅-alkoxy, phenoxy, C₁–C₄-alkyl-, C₁–C₄-alkoxy - or halogen-substituted phenoxy, phenylsulfonyl, C₁–C₄-alkyl- or halogen-substituted phenylsulfonyl, pyrrolidino, piperidino, morpholino, 2-(pyrrolidino, piperidino or morpholino)-cyclopent-1-en-1-yl or -cyclohex-1-en-1-yl, cyclohexane-1,3-dion-2-yl which is unsubstituted or monosubstituted or disubstituted in ring position 5 by C₁–C₄-alkyl, benzoylmethyl, cyano, nitromethyl, 2,4,6-trihydroxypyrimid-5-yl, 1-phenyl-3-methylpyrazol-5-on-4-yl, 5-hydroxy-3,4-dichlorofuran-2-yloxy, or the radical $$-CH\underset{Z}{\overset{Y}{\diagup}}$$

where Y and Z are identical or different and each is independently acetyl, benzoyl, C₁–C₅-alkoxycarbonyl or cyano, and if Y is cyano Z can also be methyl, and where the ring A may be fused with a benzo ring or substituted by C₁–C₄-alkyl, chlorine or bromine or, in ring position 7, by hydroxyl, C₁–C₄-alkoxy, C₁–C₅-mono- or di-alkylamino which in turn may be substituted by chlorine or phenyl, pyrrolidino, piperidino or morpholino,
R⁵ being C₁–C₈-alkyl, C₁–C₈-alkoxy, which each may be substituted by phenyl, or being C₅–C₇-cycloalkyl, C₅–C₇-cycloalkoxy, C₁–C₄-mono- or di-alkylamino, phenylamino or N-(C₁–C₄-alkyl)-N-phenylamino,
R⁶ being the radical

[benzopyran ring A with =CH–R¹, R²; O–C(R⁴)=CH–[phenyl]–W—L—W—]

or

[benzopyran ring A with =CH–R¹; O–C(R²)(R⁴)–CH–[phenyl]–W—L—W—]

where R¹, R², R⁴ and the ring A each have the above-mentioned meanings, W is oxygen, or C₁–C₄-alkylimino, and L is C₂–C₆-alkylene or
R⁷ being C₁–C₄-alkyl and
n being 2 or 3, with the proviso that when the ring A is unsubstituted and no benzofused and R¹ is methyl and X is the radical $$\overset{\backslash}{C}=CH-\underset{\underset{CO-C_6H_5}{\overset{|}{CO-CH_3}}}{\overset{|}{CH}}-[phenyl]-W-CH_2-$$

[second structure with H₃C, benzopyran O, CH₂—W—phenyl—CH—CH with CO—CH₃ and CO—C₆H₅ branches]

W is not ethylimino.

* * * * *